United States Patent [19]

Millar

[11] Patent Number: 4,957,111
[45] Date of Patent: Sep. 18, 1990

[54] METHOD OF USING A DOPPLER CATHETER

[75] Inventor: Huntly D. Millar, Houston, Tex.

[73] Assignee: Pfizer Hospital Products Group, Inc., New York, N.Y.

[21] Appl. No.: 248,777

[22] Filed: Sep. 23, 1988

Related U.S. Application Data

[63] Continuation of Ser. No. 943,446, Dec. 16, 1986, Pat. No. 4,889,128, and a continuation of Ser. No. 775,857, May 19, 1987, Pat. No. 4,665,925.

[51] Int. Cl.$^5$ .............................................. A61B 8/12
[52] U.S. Cl. .............................................. 128/662.06
[58] Field of Search ...................... 128/660.03, 662.03, 128/662.04, 662.06

[56] References Cited

U.S. PATENT DOCUMENTS 4,589,419  5/1986  Laughlin et al. ............... 128/660.03
4,794,931  1/1989  Yock .............................. 128/660.03
4,821,731  4/1989  Martinelli et al. ............. 128/660.03

Primary Examiner—Francis Jaworski
Attorney, Agent, or Firm—Peter C. Richardson; Robert F. Sheyka; Thomas C. Naber

[57] ABSTRACT

A steerable catheter having a Doppler crystal at the tip to measure the velocity of blood in vivo—and inferentially the blood flow. The catheter includes two passageways, one passageway being exposed to the blood stream with the other passageway containing the electrical leads to the Doppler crystal. The one passageway is dimensioned for receiving a wire guide for accurately manipulating the catheter. Preferably, the catheter incorporates an inflatable angio-balloon operable to distend the blood vessel in the region of a stenosis. Thus, blood flow can be determined in the region of the stenosis before and/or after the vessel is distended. The passageways are preferably defined by a pair of generally concentric tubes with the Doppler crystal doughnut-shaped and sealingly disposed at the tip of the catheter.

5 Claims, 1 Drawing Sheet

METHOD OF USING A DOPPLER CATHETER

This application is a continuation of Ser. No. 943,446 filed Dec. 16, 1986 and now U.S. Pat. No. 4,889,128, and a continuation of Ser. No. 775,857 filed May 19, 1987 and now U.S. Pat. No. 4,665,925.

BACKGROUND OF THE INVENTION

1. Field of the Invention

This invention broadly relates to a catheter-like device and method for measuring in vivo the velocity of a biological fluid, such as blood. In particular, it relates to a velocity measuring, Doppler crystal, steerable catheter which incorporates an angioplasty, expandable balloon for identifying and treating arterial stenoses.

2. Description of the Prior Art

Coronary artery disease is quite common and is usually manifested in a constriction or stenosis in the arterial tree. An inability to adequately increase flow coronary artery disease. Coronary vasodilator reserve or maximum coronary blood flow is a key indicator of the adequacy of the arterial tree. That is, the coronary vasodilator reserve correlates to the ability of the arterial tree to respond to an increase in myocardial oxygen demand. Hyperemic response or increased blood flow caused by vessel dilation has long been used as a measure of coronary vasodilator reserve. Progressive coronary artery disease can lead to increased vessel stenosis, selective lesions and gradual diminution of the reactive hyperemic response.

Since the ability to adequately analyse changes in blood flow through stenosed coronary arteries is important in properly evaluating the extent of coronary artery disease, many diagnostic tests have been devised to identify the flow limiting characteristics of a particular stenosis. The most common procedure used to predict the physiologic importance of a coronary stenosis is the use of the coronary arteriogram. Such a coronary arteriogram (or angiogram) involves the injection of a radiopaque material (angiodye) into the arterial tree and subsequent radiographic analysis of the extent of the stenosis. Such angiographic analysis is often undertaken concurrent with the inducement of a hyperemic response. Typically, the angiodye induces a certain degree of hyperemic response with other pharmacological agents (e.g. dipyridamole, meglumine diatrizoate, etc.) often used to increase the degree of hyperemia.

Such arteriographic prediction of the effect of coronary arterial disease has recently been criticized for its erratic reliability. For example, interobserver variability error has been shown to be sometimes significant in arteriograph analysis. Further, arteriograph analysis involves a longitudinal cross-sectional view of the vessel in question and usually compares the region in question with the immediately adjacent vessel region. This protocol assumes that the region of the vessel adjacent the lesioned section is normal. Of course, this assumption is often incorrect in that the adjacent region of the vessel may have moderate to severe stenosis which would be readily apparent on a histological or cross-sectional view of the vessel.

In fact, in a recent study (White, et al., *Interpretation of the Arteriogram*, 310 New Eng. J. Med. 819-824, (1984)) the authors found no significant correlation between the angiographically determined percentage of coronary obstruction and the hypermic response. Thus, it was concluded that the coronary arteriogram often provides inaccurate information regarding the physiological consequences of the coronary artery disease.

Still other researchers have concluded that the arteriogram is only reliable in identifying a stenosis with greater than about 80% construction of the vessel. However, marked impairment of the coronary vasodilator reserve can also occur in the 30-80% constriction range, but such stenoses are often not identified by the arteriogram. Thus, while the coronary arteriogram is useful in giving anatomic definition to coronary occlusions, it often provides little information concerning the hemodynamic consequences until near total occlusion of the vessel occurs.

In light of the shortcomings of arteriographic prediction, other methods have been proposed to more accurately analyze coronary stenosis. For example, computerbased quantitative coronary angiographic, coronary videodensitometery and radionuclide-perfusion techniques have all been employed. However, all of the techniques present other difficulties as prediction tools. For example, radionuclide techniques measure regional blood flow, but do not permit continuous assessment of coronay blood flow and are only accurate at low blood flow rates.

In response to the serious drawbacks with current analytical methods employed in assessing the physiological effects of coronary arterial disease, several researchers have experimented with utilizing a catheter which incorporates a Doppler mechanism to measure in vivo the blood velocity (and inferentially blood flow rate). For example, G. Cole and C. Hartley in *Pulsed Doppler Coronary Artery Catheter*, 56 Circulation 18-25 (1977) proposed a pulse Doppler crystal fitted at the end of a catheter for in vivo analysis. Similarly, Wilson, et al., *Diagnostic Methods*, 72 Circulation 82-92 (1985) proposed a catheter having a radially-oriented Doppler crystal.

Doppler techniques for measuring flow are advantageous because rapid and dynamic changes in flow can be detected, real-time recordings can be obtained and such techniques are adaptable for miniaturization. In fact, past studies with Doppler catheters appear to have validated the accuracy of such Doppler measurements as an indication of flow. These studies contend that the obstruction of blood flow caused by the catheter is insignificant and that the velocity measurements obtained art linearly related to the actual flow rates. Further, these velocity measurements purportedly accurately track actual flow rates throughout hyperemic response.

To date, however, such Doppler catheters are largely impractical for clinical applications and are beset with technical difficulties. For example, such past Doppler catheters have been of such a size that stenoses located in most parts of the arterial tree cannot be effectively evaluated. Further, such past Doppler-based catheters have not been effectively steerable and thus cannot be accurately placed within the arterial tree. In fact, signal instability and error has been often encountered due to catheter placement and orientation relative to the vessel walls and flow axis. Of course, of primary consideration in a Doppler-based catheter design is the safety to the patient by the electrical isolation of the Doppler crystal.

SUMMARY OF THE INVENTION

The problems outlined above are largely solved by the steerable, catheter-like, velocity-measuring device and method of the present invention. The device hereof is achieved on a very small scale—approximately number three French (.039 inch diameter)—for placement in many locations previously unattainable in the arterial tree. The device is designed to accept a conventional wire guide, which enables the steerable placement of the device at a desired location. In one embodiment, the device incorporates an inflatable angio-balloon which enables treatment of stenosis and analysis of the blood velocity through this stenosis without withdrawal of the catheter-like device.

Broadly speaking, the catheter-like device includes an elongated, flexible body having first and second passageways longitudinally oriented within the body with a Doppler mechanism attached adjacent the distal end of the body for determining the velocity of a biological fluid. The Doppler mechanism includes electrical leads operably disposed within one of the passageways, while the other passageway is adapted for exposure to the biological fluid. Preferably, the body is tubular with an inner channel structure operably receives within the body to define and separate the two passageways. The Doppler attached adjacent the distal end of the body.

In a preferred form the inner channel is tubular and coaxially aligned within the body to define a central lumen within the channel and an annular lumen between the channel and body. In this embodiment the Doppler crystal is a generally flat, annular, doughnut-shaped piezoelectric ceramic having a central aperture through which the channel extends. The Doppler crystal is sealingly attached adjacent the distal end of of body. The electrical leads are received in the annular lumen in isolation from the biological fluid. The central lumen is not only adapted for receiving a steerable wire guide, but can equally be used to inject pharmacological agents or angiodye into the arterial tree.

In a preferred embodiment, an expansion means is operably coupled to the body and in operable for selectably exerting outward pressure against the vessel. Preferably, a pneumatic passageway extends longitudinally through the body. The expansion means preferably includes a flexible, balloon-like sleeve coupled to the pneumatic passageway which is selectably outwardly expandable to occlude or distend a portion of the blood vessel.

The device of the present invention lends itself to a method of identifying and treating stenoses in the arterial tree, particularly when utilizing the embodiment of the device which incorporates an angio-balloon proximate to the distal end of the device. With a wire guide received in the device, the catheter-like device is easily inserted and steerable in the arterial tree. The wire guide is manipulated to position the catheter in the region of a stenosis. With the device in place, the Doppler crystal is utilized to measure the velocity of the blood in the region of the stenosis. The Doppler crystal can be operated to determine the velocity of the blood both before and after the angio-balloon is expanded in the region of the stenosis. One optical is to expand the angio-balloon to distend the arterial vessel in the region of the stenosis, in a manner similar to conventional angioplasty techniques. Another option is to expand the angio-balloon only to the extent of occluding the vessel for a short period of time to induce a hyperemic response. Of course, the Doppler mechanism continuously provides velocity measurements throughout a hyperemic response.

DESCRIPTION OF THE PREFERRED EMBODIMENTS

Figure 1:
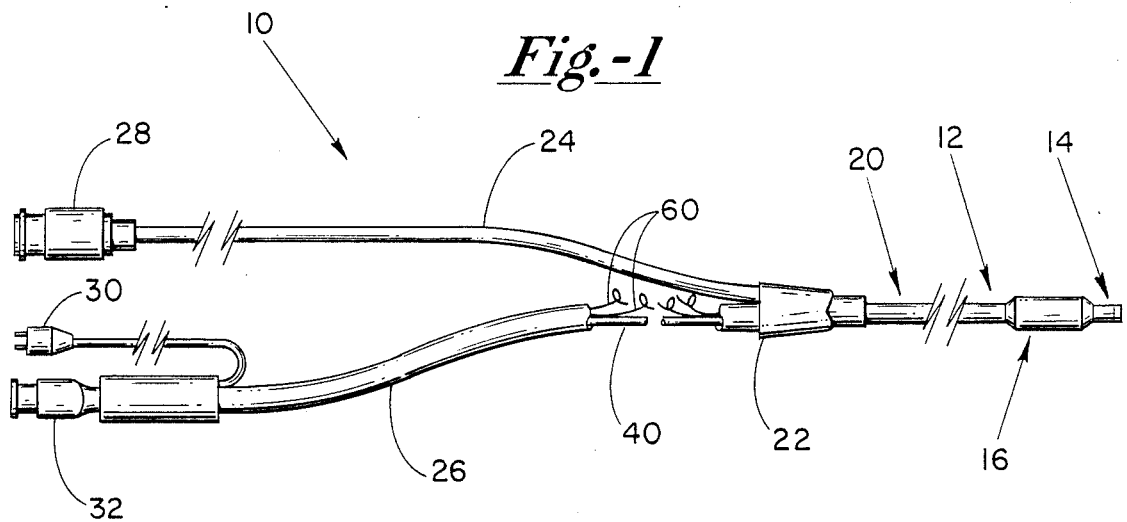
FIG. 1 is a fragmentary view with some parts broken away for clarity, of the preferred embodiment of the device of the present invention.

Turning now to the drawing, a velocity measuring, catheter-like device 10 in accordance with the present invention is illustrated. Broadly speaking the device 10 includes an elongated, flexible, tubular body 12, Doppler mechanism 14, and expansion means 16. The device 10 is dimensioned and adapted for insertion in vivo into the arterial tree of a patient.

In more detail, the body 12 includes a distal section 20 extending between the Doppler mechanism 14 and a branch connector 22. Dividing from the branch connector 22 towards the proximal end is a pneumatic section 24 and a section 26 (lower left portion of FIG. 1). The pneumatic section 24 terminates in a Luer fitting 28 which is adapted for connection to a selectable pneumatic source. Section 26 terminates in a Doppler electrical connector 30 joined to the section 26 and a multipurpose Luer fitting 32.

Figure 2:
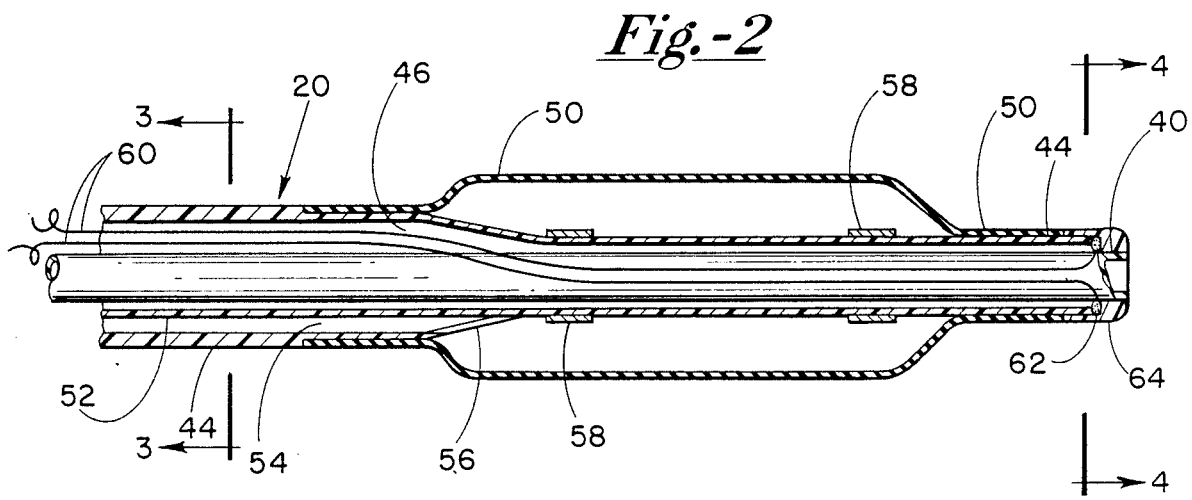
FIG. 2 is an enlarged, fragmentary, longitudinal view in partial section of the distal end of a device in accordance with the present invention.

A flexible, elongated, inner tubular channel 40 extends from the Luer fitting 32 (FIG. 1) through the distal section 20 (see FIG. 2). The tubular, infusion channel 40 defines a central, infusion lumen 42 (see FIGS. 3, 4). Turning to FIG. 2, the distal section 20 includes an outer flexible tube 44 which, towards the distal end, converges inwardly into closely spaced relation to the inner channel 40. The annular region between the inner walls of the tube 44 and outer walls of the channel 40 defines annular lumen 46 (see FIGS. 2-3).

Figure 3:
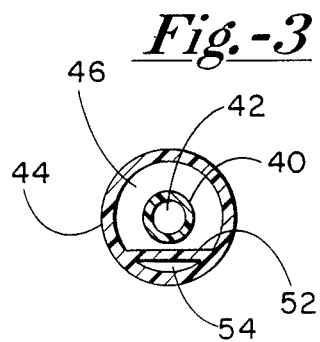
FIG. 3 is a sectional view taken along line 3—3 of FIG. 2.
Figure 4:
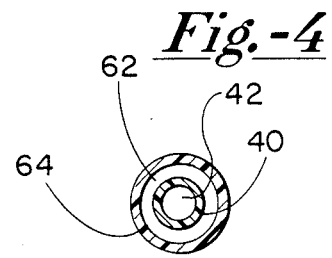
FIG. 4 is a sectional view taken along line 4—4 of the device illustrated in FIG. 2.

The expansion means 16 includes an expandable flexible balloon-like sleeve 50 sealingly fitted circumferentially to the outer tube 44 as shown in FIG. 2. As illustrated in FIGS. 2-3, and a chord structure 52 longitudinally extends through the distal section 20 between the sleeve 50 and branch connector 22. The chord structure 52 and a portion of the inner wall of the tube 44 (see FIG. 3) defines a pneumatic passageway 44 which is operably connected between the sleeve 50 and pneumatic section 24. An aperture 56 through the tube 44 (FIG. 2) connects the passageway 54 with the interior of the sleeve 50. A pair of radiopaque ring markers 58 are operably disposed about the tube 44 inside of the sleeve 50.

In more detail, the Doppler mechanism 14 incorporates a pair of electrical leads 60 operably connected to the electrical connector 30 and passing through the section 26 (see FIG. 1) and into the distal section 20 (see FIG. 2). As shown in FIG. 2, the electrical leads 60 are disposed in the annular lumen 46 defined by the region between the channel 40 and tube 44 (see FIGS. 2-3). The Doppler leads 60 terminate at the washer-like, flat, doughnut-shaped Doppler crystal 62 which is sealingly disposed about the channel 40. The Doppler crystal 62 in the preferred embodiment is a piezoelectric ceramic crystal comprising a lead-zirconate-titanate material which is about 0.003 inch in thickness and 0.035 inch in outside diameter. The Doppler crystal 62 is designed to resonate at 20 megaHertz with a voltage applied to generate a 20 megaHertz signal (acoustic tone). The crystal 62 is a single crystal to operate as a pulsed Doppler transducer, acting alternately as a transmitter and receiver.

An encapsulant 64 is sealingly, disposed about the Doppler crystal 62. As shown in FIG. 2, the tip of the channel 40 extends slightly past the marginal periphery of the tube 44 and past the crystal 62, which in combination with the encapsulant 64 provides effective isolation of the Doppler crystal 62 and leads 60 from the biological fluid when in use in the arterial tree.

The principal of pulsed Doppling operation in measuring velocity of a fluid is known in the art, for example as explained by C. Hartley and J. Cole in *Pulsed Doppler Flow Measurement*, 37 J. of App. Phys. 626–629 (1974) (incorporated by reference herein). In the embodiment illustrated in the drawing, the Doppler crystal 62 is single piezoelectric ceramic crystal having a master oscillator frequency of 20 megaHertz and is pulsed at a repetition frequency (prf) of 62.5 kiloHertz. Each pulse is approximately one-half microsecond in duration.

Those skilled in the art will appreciate that with the device 10 in place in the arterial tree, each acoustic tone burst is transmitted through the blood and reflected by various structures, for example red blood cells, vessel wall, plaque, etc. Depending on the distance of each reflecting structure, the returning acoustic signals received by the Doppler crystal 62 are separated in time. An adjustable receiver gate is incorporated to select signals reflected from the structures at a specified distance from the crystal 62. The reflected signals received by the Doppler crystal 62 are amplified and compared in phase and frequency to the master oscillator signal of 20 megaHertz.

The difference in frequency between the amplified reflected signal and the master oscillator signal is the Doppler shift. The Doppler shift ( f) is defined by the Doppler equation:

$$F = 2F_c {}^V\!\cos O$$

where F is the transmitted frequency; V is the velocity of the fluid: c is velocity of sound in the fluid; and 0 is the angle between the fluid flow and the acoustic axis. Since transmitted frequency (F), velocity of sound in the fluid (c), and the angle (O) are constant, the Doppler shift ( f) is linearly related to the velocity of the fluid (V). This assumes that the device 10 is in a stable position in the arterial tree and that the angle (0) remains constant. As used in the present application the term "velocity" or "velocity of the fluid" means either the absolute velocity or a number linearly related to the absolute velocity.

ALTERNATIVE EMBODIMENTS

Those skilled in the art will appreciate that many structural alternatives exist to the preferred embodiment illustrated in the drawing. For example, in a broad sense, the device 10 need not incorporate the expansion means 16 to be useful in the diagnosis coronary artery disease. In fact, prototypes have been constructed using a USCI (U.S. Catheters and Instruments) Rentrop reperfusion catheter with the Doppler mechanism 14 attached to the tip. These prototypes incorporated a 4 French outermost tubular main body (1.3 millimeters) which tapered to a tip 3 French in size (1 millimeter). The catheter was 110 millimeters long having an internal diameter of 0.020 inches running the length thereof. An internal channel tubing was fitted within this body and had a 0.018 inch outside diameter to define an annular lumen between the channel and body. The inner diameter of the inner channel was 0.0155 inches and defined an infusion or central lumen. A 0.014 inch wire guide was receivable in the central lumen. The electrical leads ran in the annular lumen with a Doppler crystal mounted at the tip of the catheter. The Doppler crystal in the prototype comprised a thin disc about 0.003 inches thickness with an outside diameter of 0.035 inches. An aperture of about 0.022 inches was centrally located to give the Doppler crystal a doughnut-shaped configuration. The Doppler crystal was interfitted over the channel and insulated and attached by epoxy between the channel and body. The channel terminated just beyond the Doppler crystal at the distal tip of the catheter.

Still other alternative exists. In the preferred device illustrated in the drawing the Doppler crystal 62 is attached at the distal tip of device 10 and axially oriented. This installation and orientation has been found preferable in giving good signal stability and accuracy. As an alternative, the Doppler crystal 62 can be installed in a more radial or oblique orientation. However, it is speculated that a radial orientation might provide inherent inaccuracies due to placement of the device in the arterial vessel with the crystal adjoining the vessel wall. Measurement of the fluid velocity would, of course, be impossible under these circumstances. Additionally, it is deemed preferable to have the acoustic axis generally linearly aligned with the fluid flow axis as compared with the oblique angle produced if the Doppler crystal 62 is radially oriented relative to the body 12. Doppler shift is usually more accurately determined with the axes aligned.

Still other alternatives exits in the precise configuration of the device 10. For example, the device 10 of the preferred embodiment envisions a catheter-like device similar to a conventional angioplastic catheter which incorporates the Doppler mechanism. However, it is anticipated that the device 10 of the present invention may be incorporated into a mechanism resembling a steerable wire guide having the Doppler mechanism at the tip, which might be inserted through a catheter when it is desired to take the velocity measurements.

As another alternative, it will be readily appreciated that the inner and outer dimensions of the channel 40 and tube 44 are not critical. This is, the outer surface of the channel 40 and inner surface of the tube 44 may in fact be adjoining with the electrical leads 60 compressed therebetween. Alternatively, the electrical leads 60 may be incorporated integral with either the channel 40 or tube 44.

As still another alternative, those skilled in the art will appreciate that the electrical leads 60 can be routed through other passages out of possible contact with the biological fluid. For example, (see FIG. 3) the electrical leads 60 could be routed through the pneumatic passageway 54 with or without the channel 40 or sleeve 50 incorporated in the device.

OPERATION

In use, the device 10 is inserted into the arterial tree through a Judkins-type guiding catheter. The device 10 is preferably preloaded with a teflon-coated steerable guidewire (e.g. 0.014 inch O.D. USCI-type) through the central lumen 42. After passing the guidewire/device 10 combination through the guiding catheter to the coronary ostium, the guidewire is used to selectively place the distal end of the device 10 proximate to the coronary stenosis under study.

It is assumed that this operation takes place in a conventional cardiac catheterization laboratory. It is important throughout the velocity measurements to insure that the distal tip of the device 10 remains in a generally stable position. When initially positioning the distal tip, small injections of an angiodye may be injected through the Luer fitting 32 into the central lumen 42 into the bloodstream to verify the position of the distal tip. Doppler measurements are then taken with the range gate adjusted and the position of the distal tip varied to obtain the maximum velocity signal After the position of the distal tip of the device 10 is verified and stabilized, the guidewire can be withdrawn from the device 10. In any event, after the initial velocity measurements are made, a hyperemic response will typically be induced to effectively analyze the coronary vasodilator reserve capacity. Several methods are available for inducing the hyperemic response. In the preferred method, the sleeve 50 is expanded in the area of the stenosis until occlusion of the vessel is obtained. Advantageously, the Doppler mechanism 14 operates to verify the occlusion. The occlusion is held for approximately 20 seconds then released; this technique has been found to induce a hyperemic response. Other techniques are of course available. For example, a pharmacological agent such as dipyridamole or meglumine diatrizoate may be injected to induce the hyperemic response. As a third alternative, contrast media or angiodye injection will in most cases induce a sufficient hyperemic response for proper analysis.

At some stage, coronary angioplasty can be performed by expanding the sleeve 50 to dilute or distend the vessel. Of course, conventional angiographic assessment of the efficacy of the dilation can be utilized or alternatively, the dilation can be performed at progressively increasing pressures and the effectiveness analyzed by the velocity measurements. For example, before and, after the first dilation by the expansion means 16, the Doppler mechanism 14 can be operated to determine the blood flow velocity before and after the dilation and hence the efficacy of the dilation. Subsequent dilations can be made as needed.

It will be appreciated that the device 10 of the present invention is a significant advance over previous in vivo coronary catheters and allows for a significant advance in the diagnosis and treatment of coronary arterial disease. The criticisms of the use of conventional coronary arteriograms as a method of measuring the extent of coronary stenosis is, to some extent, valid. As previously discussed, some studies suggest that conventional arteriograms are particularly inaccurate where the stenosis is less than approximately an 80% occlusion. In all cases, it should be readily apparent that an apparatus which more directly takes flow measurements is ideal in analyzing coronary vasodilator reserve capacity. The device 10 of the present invention provides real time analysis by providing continuous velocity measurements which are linearly related to blood flow. This is in sharp contrast to conventional angiograms which only accuracy identify regions of possible stenoses, but not the physiological importance of such stenoses.

In practice, it has been found that the velocity measurements are very accurate in evaluating the flow. That is, various studies have shown that maximal coronary reactive hyperemic response is relatively constant whether or not a catheter the size of the device 10 is present or absent in the artery being investigated. This implies that the obstruction of blood flow by the device 10 is minimal during the hyperemic response. Further, vessel diameter expansion during hyperemic response has been found to minimally affect the accuracy of the velocity measurements as an indication of flow. Additionally, the range gating of the pulsed Doppler crystal of the device 10 of the present invention allows for selective analysis of a target region a sufficient distance (approximately 2–10 mm) away from the catheter tip to avoid tip induced turbulent flow which would affect the accuracy of the velocity measurements.

Utilizing the device 10 of the present invention, coronary artery disease is more effectively identified and treated than by use of conventional methods and devices. When used in conjunction with conventional angiograms and angioplasty procedures, the device and method of the present invention present a significant advance in the art.

I claim:

1. A method of treating stenosis in the arterial tree comprising the steps of:
   providing a catheter having a Doppler crystal attached at the distal tip thereof and axially oriented therewith, an angio-balloon proximate to the distal end, and a passageway disposed for operable contact with the blood stream;
   placing a wire guide in the passageway;
   inserting the catheter into the arterial tree;
   manipulating the wire guide to position the catheter in the region of the stenosis;
   expanding the angio-balloon in the region of the stenosis; and
   operating the Doppler crystal to measure the velocity of the blood in the region of the stenosis.

2. A method of treating stenosis in accordance with claim 1, wherein velocity measurements are taken before and after the angio-balloon is expanded.

3. A method of treating stenosis in accordance with claim 1, including the steps of:
   providing said catheter with said passageway extending substantially along the entire length of the catheter;
   withdrawing the wire guide from said passageway;
   injecting angio-dye through said passageway into the arterial tree.

4. A method of treating stenosis in accordance with claim 1, the expanding step including:
   occluding the blood vessel to induce a hyperemic response.

5. A method of treating stenosis in accordance with claim 1, the expanding step including:
   dilating the blood vessel to decrease the effects of the stenosis.

* * * * *